United States Patent
Smith

(10) Patent No.: US 6,391,925 B1
(45) Date of Patent: May 21, 2002

(54) LIQUID PHENOLIC COMPOSITION

(75) Inventor: Kim R. Smith, Woodbury, MN (US)

(73) Assignee: Ecolab Inc., St. Paul, MN (US)

( * ) Notice: Subject to any disclaimer, the term of this patent is extended or adjusted under 35 U.S.C. 154(b) by 0 days.

(21) Appl. No.: 09/482,253

(22) Filed: Jan. 13, 2000

(51) Int. Cl.$^7$ .......................... A01N 35/00; A01N 31/08
(52) U.S. Cl. ................... 514/732; 504/161; 514/733; 514/736; 514/737; 568/744; 568/746; 568/747; 568/774; 568/775
(58) Field of Search ..................... 504/161; 514/732, 514/733, 736, 737; 568/744, 745, 746, 747, 774, 775

(56) References Cited

U.S. PATENT DOCUMENTS

| | | | |
|---|---|---|---|
| 3,538,217 A | 11/1970 | Dewar et al. | 424/173 |
| 3,753,777 A | 8/1973 | Thomsen et al. | 134/6 |
| 3,824,190 A | 7/1974 | Winicov et al. | 252/106 |
| 3,997,460 A | 12/1976 | Sirine et al. | 252/106 |
| 4,157,977 A | 6/1979 | Dewar et al. | 134/6 |
| 4,759,867 A | 7/1988 | Choy et al. | 252/143 |
| 4,853,411 A | 8/1989 | Clarkson et al. | 514/441 |
| 5,227,360 A | 7/1993 | Sherba et al. | 504/152 |
| 5,298,252 A | 3/1994 | Hagiwara et al. | 424/409 |
| 5,646,105 A | 7/1997 | Hachmann et al. | 510/382 |
| 5,756,500 A | 5/1998 | Beilfuss et al. | 514/245 |

FOREIGN PATENT DOCUMENTS

| | | |
|---|---|---|
| GB | 1 226 338 | 3/1971 |

OTHER PUBLICATIONS

Bayer Material Safety Data Sheet, *Bayer Corporation Product Safety & Regulatory Affairs*, MSDS for 300038, Bayer Product Code N–111, 9 pages (Mar. 26, 1997).

Bayer Material Safety Data Sheet, *Bayer Corporation Product Safety & Regulatory Affairs*, MSDS for 300210, Bayer Product Code N–115, 9 pages (Mar. 26, 1997).

Bayer Product Information for Preventol BP Technical, 1 page (Date Unknown).

Bayer Product Information for Preventol O extra, 1 page (Date Unknown).

NIPA Hardwicke Inc. Material Safety Data Sheet, *NIPA Hardwicke Inc.*, MSDS for 300228, 3 pages (Mar. 20, 1997).

NIPA Hardwicke Inc. Product Information of NIPACIDE®PTAP, 1 page (Date Unknown).

*Primary Examiner*—Peter O'Sullivan
(74) *Attorney, Agent, or Firm*—Merchant & Gould P.C.

(57) ABSTRACT

A liquid composition of phenolic compounds can be formed in the substantial absence of a solvent and a surfactant. This composition includes at least one substituted phenol and a halo-substituted phenol. In one embodiment, the composition includes benzylchlorophenol and at least one of phenylphenol and tert-pentylphenol. In another embodiment, the composition includes benzylchlorophenol, phenylphenol, and tert-pentylphenol. The composition may be useful for preparing an antimicrobial material. A liquid phenolic composition can be prepared by forming a composition having at least one substituted phenol and a halo-substituted phenol in the substantial absence of a solvent and surfactant and mixing the composition until a liquid phenolic composition is formed. Alternatively, a liquid phenolic composition can be prepared by heating at least one substituted phenol in the substantial absence of a solvent and a surfactant to form a liquid substituted phenol, heating a halo-substituted phenol in the substantial absence of a solvent and surfactant to form a liquid halo-substituted phenol, combining the at least one liquid substituted phenol and the liquid halo-substituted phenol, and cooling the mixture to about ambient temperature.

34 Claims, 1 Drawing Sheet

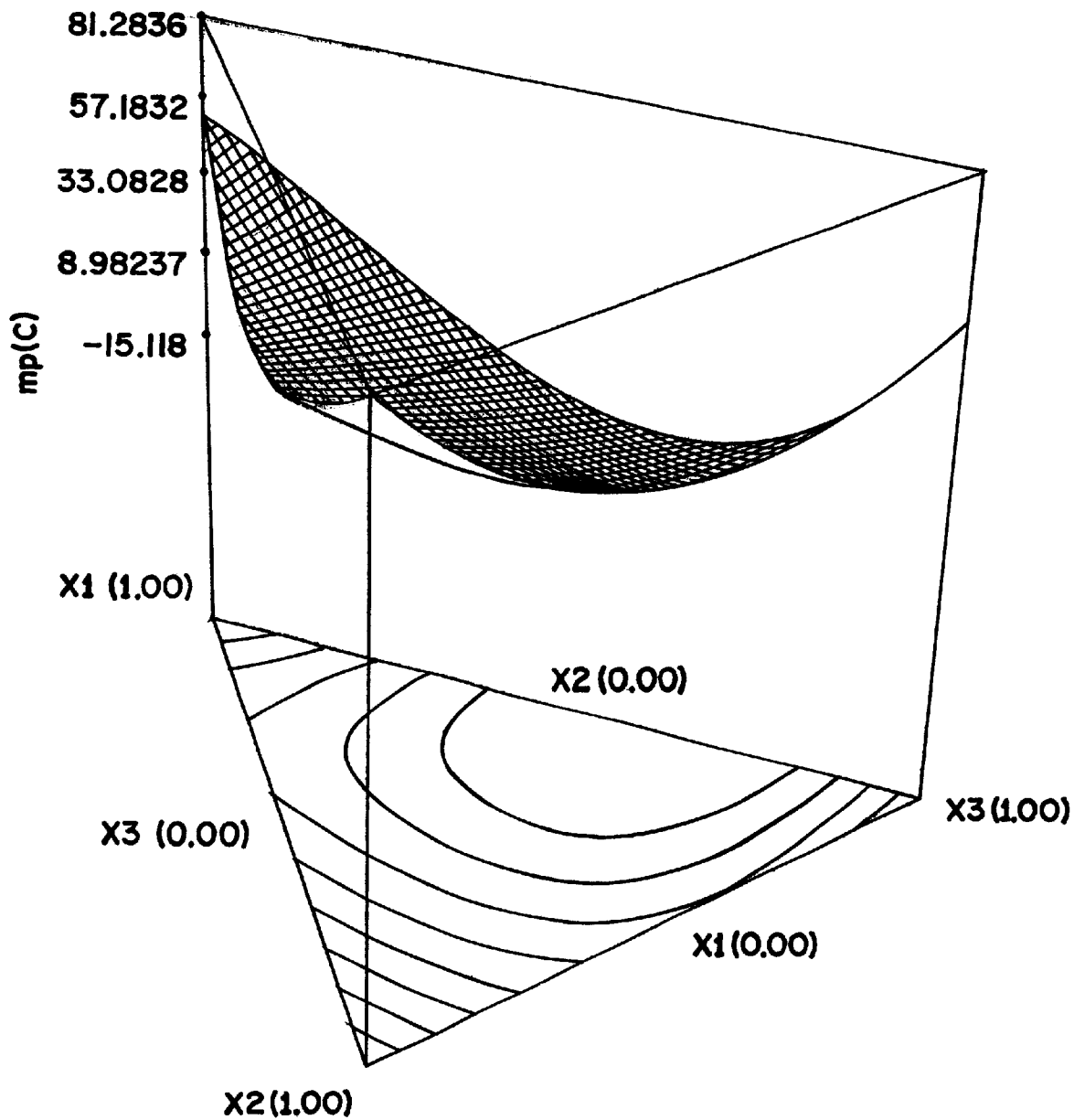

LIQUID PHENOLIC COMPOSITION

FIELD OF THE INVENTION

The invention relates to liquid phenolic compositions that are substantially free of a solvent and a surfactant and that are prepared from phenolic compounds that are typically solids at ambient temperature. These compositions can be easily prepared, handled, stored, and formulated into useful materials, particularly aqueous antimicrobial materials.

BACKGROUND OF THE INVENTION

Antimicrobial formulations that contain phenolic compounds are known in the art and are commercially valuable for the reduction of microbial populations on surfaces. These compositions contain active antimicrobial phenolic materials and a variety of other ingredients such as anionic surfactants, abrasives, solvents, acidic materials, and other compositions common for antimicrobial compositions for use on surfaces.

The addition of crystalline or powdered phenolic compounds into a formulation requires the handling and transfer of a dusty solid during the production process. This exposes production personnel to phenolic dust released into the air during the transfer process. Exposure to the dust of phenolic compounds has been known to result in respiratory-tract irritation, skin irritation, eye burns, depigmenting skin, digestive-tract burns, etc. In particular, repeated exposure to phenolic compounds may result in, for example, allergic sensitization, conjunctivitis, etc.

Thus, a substantial need exists for a liquid form of a phenolic compound that can be substituted for dusty crystalline or powdered phenolic compounds. Moreover, it would be advantageous if such liquid phenolic compounds did not contain a solvent or surfactant, thereby avoiding the problem of altering or adulterating the formulation into which the compounds are incorporated. Such formulations are highly regulated under the Federal Insecticide, Fungicide, and Rodenticide Act, which prohibits the adulteration of antimicrobial formulations without going through a lengthy testing and approval process.

BRIEF DESCRIPTION OF THE FIGURES

FIG. 1 shows a surface representation of a formula that defines the parameters of a liquid composition material made from naturally solid phenolics.

DETAILED DESCRIPTION OF THE INVENTION

The present invention provides for a liquid phenolic composition substantially free of a solvent and a surfactant, methods for preparing a liquid phenolic composition, and methods for preparing a formulation that includes a liquid phenolic composition of the invention.

The liquid compositions of the present invention include phenolic compounds and are substantially free of a solvent and a surfactant. The term "liquid" as used herein includes a composition that is liquid at about ambient temperature (typically understood to be about 23° C. to about 27° C.) and pressure and does not freeze until cooled to a temperature of at least about 20° C., preferably 10 °C., and more preferably 0° C. The term "substantially free of a solvent and a surfactant" refers to the liquid phenolic composition not having a solvent or surfactant in an amount to dissolve substantially the phenolic compounds. That is, the liquid form of the phenolic compounds is created and maintained by the interaction of the phenolic compounds and not by the addition of a surfactant or a solvent for that purpose. One skilled in the art would appreciate that small amounts of materials commonly known to have solvent or surfactant properties can be added to the composition of the invention and can serve some function other than to dissolve the phenolic compounds.

The compositions of the invention contain at least one substituted phenol and at least one halo-substituted phenol. One liquid phenolic composition of the invention includes a substituted phenol of the formula:

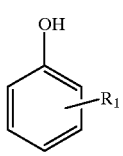

(I)

in which $R_1$ is aryl, aralkyl, $C_{1-24}$ alkyl, or $C_{2-24}$ alkenyl; and a halo-substituted phenol of the formula:

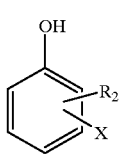

(II)

in which $R_2$ is aryl, aralkyl, $C_{1-24}$ alkyl, or $C_{2-24}$ alkenyl; and X is halo, preferably chloro or bromo.

The term "aryl" includes an aromatic hydrocarbyl, including fused aromatic rings, such as, for example, phenyl and naphthyl. Such groups may be unsubstituted or substituted on the aromatic ring by, for example, $C_{1-4}$ alkyl, $C_{1-4}$ alkoxy, amino, hydroxy, or acetyloxy.

The term "aralkyl" includes alkyl as defined above that is substituted on the aromatic ring by $C_{1-4}$ alkyl, such as, for example, benzyl. The term "alkyl" is as described below. The alkyl substitution serves as the bonding linkage between aryl and phenol.

The term "$C_{1-24}$ alkyl" includes a linear or branched saturated aliphatic hydrocarbon chain having from one to twenty-four carbon atoms, such as, for example, methyl, ethyl, propyl, isopropyl (1-methylethyl), butyl, tert-butyl (1,1-dimethylethyl), pentyl, tert-pentyl, and the like. Preferably alkyl is $C_{1-12}$ alkyl.

The term "$C_{2-24}$ alkenyl" includes an unsaturated aliphatic hydrocarbon chain having from two to twenty-four carbon atoms, such as, for example, ethenyl, 1-propenyl, 2-propenyl, 1-butenyl, 2-methyl-1-propenyl, and the like.

The above alkyl or alkenyl groups may optionally be interrupted on the chain by a heteroatom, such as, for example, a nitrogen or oxygen atom, forming an alkylaminoalkyl or alkoxyalkyl, for example, methylaminoethyl or methoxymethyl.

The term "halo" includes fluoro, chloro, and bromo.

The substituted phenol of formula I may be, for example, benzylphenol, phenylphenol, naphthylphenol, methylphenylphenol, ethylphenylphenol, methylnaphthylphenol, methylphenol, ethylphenol, propylphenol, butylphenol, tert-butylphenol, pentylphenol, tert-pentylphenol, and the like. For example, the substituted phenol may be 2-phenylphenol, 4-phenylphenol, or a mixture thereof. The substituted phenol also may be 2-tert-pentylphenol, 4-tert-pentylphenol, or a mixture thereof.

Substituted phenols of formula I known in the art to be useful for antimicrobial materials and suitable for use with compositions and methods of the invention include phenylphenol and tert-pentylphenol.

The halo-substituted phenol of formula II may be, for example, benzylchlorophenol, benzylbromophenol, phenylchlorophenol, naphthylchlorophenol and the like. For example, the halo-substituted phenol may be 2-benzyl-4-chlorophenol, 4-benzyl-2-chlorophenol, or a mixture thereof.

Halo-substituted phenols of formula II known in the art to be useful for antimicrobial materials and suitable for use with compositions and methods of the invention include 2-benzyl-4-chlorophenol and 4-benzyl-2-chlorophenol.

In one embodiment, the composition of the invention includes phenylphenol and benzylchlorophenol. In still another embodiment, the composition of the invention includes tert-pentylphenol and benzylchlorophenol.

The amount of each phenolic compound suitable for preparing a liquid phenolic composition of the invention can be determined by conducting a standard mixture experiment, which will be described below.

The composition of the invention typically can include from about 10 to 60 weight-% of a substituted phenol and from about 40 to 90 weight-% of a halo-substituted phenol.

A second phenolic composition of the invention includes a first substituted phenol of the formula:

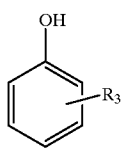

(III)

in which $R_3$ is aryl, aralkyl, $C_{1-24}$ alkyl, or $C_{2-24}$ alkenyl; a second substituted phenol, different from the first substituted phenol, of the formula:

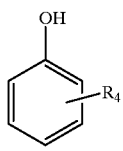

(IV)

in which $R_4$ is aryl, aralkyl, $C_{1-24}$ alkyl, or $C_{2-24}$ alkenyl; and a halo-substituted phenol of the formula:

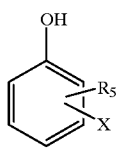

(V)

in which $R_5$ is aryl, aralkyl, $C_{1-24}$ alkyl, or $C_{2-24}$ alkenyl; and X is halo, preferably chloro or bromo.

The terms "aryl," "aralkyl," "$C_{1-24}$ alkyl," "$C_{2-24}$ alkenyl," and "halo" are as defined above.

The first substituted phenol of formula II may be, for example, benzylphenol, phenylphenol, naphthylphenol, methylphenylphenol, ethylphenylphenol, methylnaphthylphenol, methylphenol, ethylphenol, propylphenol, butylphenol, tert-butylphenol, pentylphenol, tert-pentylphenol, and the like. For example, the substituted phenol of formula III may be 2-phenylphenol, 4-phenylphenol, or a mixture thereof. The substituted phenol of formula III also may be 2-tert-pentylphenol, 4-tert-pentylphenol, or a mixture thereof. Substituted phenols of formula III known in the art to be useful for antimicrobial materials and suitable for use with compositions and methods of the invention include phenylphenol and tert-pentylphenol.

The second substituted phenol of formula IV may be, for example, benzylphenol, phenylphenol, naphthylphenol, methylphenylphenol, ethylphenylphenol, methylnaphthylphenol, methylphenol, ethylphenol, propylphenol, butylphenol, tert-butylphenol, pentylphenol, tert-pentylphenol, and the like. The second substituted phenol of formula IV can be a compound that is different from the first substituted phenol of formula III.

The substituted phenol of formula IV may be, for example, 2-phenylphenol, 4-phenylphenol, or a mixture thereof. The substituted phenol of formula IV also may be 2-tert-pentylphenol, 4-tert-pentylphenol, or a mixture thereof. Substituted phenols of formula IV known in the art to be useful for antimicrobial materials and suitable for use with compositions and methods of the invention include phenylphenol and tert-pentylphenol.

The halo-substituted phenol of formula V may be, for example, benzylchlorophenol, benzylbromophenol, phenylchlorophenol, naphthylchlorophenol, and the like. For example, the halo-substituted phenol may be 2-benzyl-4-chlorophenol, 4-benzyl-2-chlorophenol, or a mixture thereof.

Halo-substituted phenols of formula V known in the art to be useful for antimicrobial materials and suitable for use with compositions and methods of the invention include 2-benzyl-4-chlorophenol and 4-benzyl-2-chlorophenol.

In a preferred embodiment, a composition of the invention includes phenylphenol as the first substituted phenol, tert-pentylphenol as the second substituted phenol, and benzylchlorophenol as the halo-substituted phenol.

The amount of each phenolic compound suitable for preparing a liquid phenolic composition of the invention, which is substantially free of a solvent and a surfactant, can be determined by a standard mixture experiment. More particularly, the weight fraction of each phenol compound can be determined by a standard mixture experiment. A standard mixture experiment involves collecting data directed to a particular characteristic of a mixture and analyzing the data to define a relationship between the mixture components and the particular mixture characteristic. For the compositions of the invention, the characteristic of the mixture evaluated is the melting point for the liquid composition. Melting point includes a particular temperature at which the liquid mixture solidifies as well as a temperature range over which the liquid mixture solidifies. The melting points of the liquid compositions are evaluated to determine the relationship between the components that results in a liquid mixture at about ambient temperature, preferably at about 10 °C., and more preferably at about 0° C.

To carry out the standard mixture experiment, the melting points of selected phenolic compositions containing mixtures of two or more phenolic compounds are determined. For mixtures resulting in liquids, melting points are measured by cooling the liquid composition until it solidifies. The weight fraction of components and the corresponding melting points are then analyzed, typically by, for example, a computer program known in the art, such as Design Expert, to compute an equation describing the relationship between the ratio of the mixture components and the melting point. For example, the appended example illustrates that such a relationship between phenylphenol, tert-pentylphenol, and benzylchlorophenol may be represented by the formula:

$$(55.2x+83.7y+33.3z-182.1xy-213.7xz+89.6xyz) \leq 25$$

in which x is the weight fraction of phenylphenol; y is the weight fraction of tert-pentylphenol; and z is the weight fraction of benzylchlorophenol. Preferably $$(55.2x+83.7y+33.3z-182.1xy-213.7xz+89.6xyz) \leq 10.$$

A liquid phenolic composition of the invention may be prepared by first combining at least one substituted phenol and a halo-substituted phenol in the substantial absence of a surfactant and a solvent. Then the phenolic composition is mixed until the melting point of the system is sufficiently depressed that a liquid phenolic composition is formed. To increase the speed at which a composition containing crystalline or powdered phenolic compounds becomes a liquid, heat may also be applied to the composition. Liquid phenolic compositions of the invention remain liquid even when the composition is cooled to about ambient temperature, preferably even when cooled to 10° C., and more preferably 0° C.

Alternatively, a liquid phenolic composition of the invention may be prepared by initially heating each phenolic component to at least its respective melting point to form a liquid phenolic component. For example, a substituted phenol can be heated until it liquifies, and a halo-substituted phenol can be heated until it liquifies. The individual liquid phenolic components are then combined to form a liquid phenolic composition of the invention. This composition remains liquid even when cooled to about ambient temperature, preferably when cooled to 10° C., and more preferably 0° C.

The liquid phenolic compositions of the invention are prepared in the substantial absence of solvent and surfactant and can be maintained without adding solvent or surfactant.

The term "surfactant" includes nonionic, cationic, and anionic surfactants. Nonionic surfactants typically include an alkylene oxide, preferably ethylene oxide or propylene oxide, moiety. Such surfactants often include, for example, EOPO block copolymers, alcohol ethoxylates, alkyl phenol ethoxylates, and other such materials.

Anionic surfactants are commonly sodium or potassium salts of hydrophobically substituted acidic groups. Such anionic surfactants commonly include sodium salts of sulfonic acid or sulfated alcohols, sodium salts of phosphonic acids, sodium salts of carboxylic acid, and the like.

The term "solvent" includes water or nonphenolic organic liquids that act to solvate and dissolve or suspend organic materials. Such solvents often include, for example, aliphatic hydrocarbons such as hexane petroleum ether and other distillates; benzene or toluene; chlorinated hydrocarbons such as chloroform; ether solvents such as diethyl ether; and carbitol or cellosolve type materials. Other solvents include lower alkanol such as ethanol, propanol, isopropanol, butanol, etc.

A phenolic composition of the invention can contain an additive suitable for providing some function other than to dissolve the phenolic compounds. Suitable additives include, for example, antioxidants, wetting agents, viscosity modifiers, dyes, pH modifiers, fragrances, crystallization inhibitors, and the like.

Suitable antioxidants include, for example, butyl hydroxytoluene, ascorbic acid, and the like.

Suitable wetting agents include, for example, laureth-7, laurylamine oxide, dodecylbenzene sulfonate, and the like.

Suitable viscosity modifiers include, for example, anionic and cationic polymers. Such viscosity modifiers include, for example, sodium polyacrylate, sodium carboxymethylcellulose, and the like.

Suitable dyes include, for example, FDNC yellow 1, DNC Red 20, and the like.

Suitable pH modifiers include, for example, alkanolamine and the like.

Suitable fragrances include, for example, benzaldehyde, methyl salicylate, citrus, and the like.

Suitable crystallization inhibitors include, for example, glycol, glycol ether alcohol, water, and the like.

The liquid phenolic compositions of the invention are particularly advantageous because during their preparation, there is a reduced amount of handling of crystalline or powdered phenolic compounds, which results in improved worker safety. For example, the raw materials (i.e., the substituted phenols and halo-substituted phenols) may be liquified in large quantities and then the individual liquid raw materials can be transferred into a formulation or into a container for later use. This reduces or eliminates the hazard created by dust dispersed into the air when formulations are prepared from crystalline or powdered phenolic compounds.

These liquid phenolic compositions may be used to prepare a formulation that is suitable for being used as an antimicrobial product. The term "antimicrobial product" as used herein includes any material that may be used to eliminate or reduce the contamination of bacteria, protozoa, fungi, algae, viruses, etc.

A liquid phenolic composition of the invention can be added to known disinfectant formulations to prepare a formulation suitable for acting as an antimicrobial material. Such formulations are described in, for example, *Disinfection, Sterilization, and Preservation*, by Seymour S. Block (Lea & Febiger eds., 4th Edition, 1991).

This invention will be further characterized by the following examples. These examples are not meant to limit the scope of the invention, which has been fully set forth in the foregoing description. Variations within the scope of the invention will be apparent to those skilled in the art.

WORKING EXAMPLE

To determine the respective amounts of phenylphenol, tert-pentylphenol, and benzylchlorophenol that may be combined to form a liquid phenolic composition of the invention, a standard mixture experiment was conducted and the results were evaluated.

In this example, 2-phenylphenol (Bayer Corporation, Pittsburgh, Pa.), 4-tert-pentylphenol (NIPA HARDWICKE INC., Wilmington, Del.), and 2-benzyl-4-chlorophenol (Bayer Corporation, Pittsburgh, Pa.) were studied. 2-Phenylphenol has a melting point of 57° C.; 4-tert-pentylphenol has a melting point of 91 ° C.; and 2-benzyl-4-chlorophenol has a melting point of 44° C.

2-Phenylphenol, 4-tert-pentylphenol, and 2-benzyl-4-chlorophenol were combined according to the weight percents shown in Table 1 and the mixtures were mixed and warmed to a temperature of about 70° C. until a liquid mixture was formed. The mixtures were then cooled to determine when the liquid phenolic mixture would freeze.

TABLE 1

Liquid Phenolic Mixtures and Freezing Temperatures

| SAMPLE | Respect Weight Percent | | | Respective Weight (grams) | | | $T_F$ (° C.) |
|---|---|---|---|---|---|---|---|
| | 2-phenyl-phenol | 4-tert-pentyl-phenol | 2-benzyl-4-chloro-phenol | 2-phenyl-phenol | 4-tert-pentyl-phenol | 2-benzyl-4-chloro-phenol | |
| 27B | 75 | 25 | 0 | 1.50 | 0.50 | 0 | 22 |
| 27C | 50 | 50 | 0 | 1.00 | 1.00 | 0 | 35 |
| 27D | 25 | 75 | 0 | 0.50 | 1.50 | 0 | 52 |
| 27E | 75 | 0 | 25 | 1.50 | 0 | 0.50 | 35 |
| 27F | 50 | 0 | 50 | 1.00 | 0 | 1.00 | * |
| 27G | 25 | 0 | 75 | 0.50 | 0 | 1.50 | * |
| 27H | 25 | 25 | 50 | 0.5 | 0.5 | 1.00 | * |
| 27I | 25 | 50 | 25 | 0.5 | 1.00 | 0.5 | 35 |
| 27J | 50 | 25 | 25 | 1.00 | 0.5 | 0.5 | * |
| 27K | 33 | 33 | 34 | 0.66 | 0.66 | 0.68 | 28 |
| 27L | 12 | 13 | 75 | 0.24 | 0.26 | 1.50 | * |
| 27M | 12 | 75 | 13 | 0.24 | 1.50 | 0.26 | * |
| 27N | 75 | 12 | 13 | 1.50 | 0.24 | 0.26 | * |
| 28A | 0 | 75 | 25 | 0 | 1.50 | 0.50 | 55 |
| 28B | 0 | 50 | 50 | 0 | 1.00 | 1.00 | 25 |
| 28C | 0 | 25 | 75 | 0 | 0.50 | 1.50 | 20 |

* Still a liquid mixture when cooled to 0° C.

These data show several phenolic mixtures that remain liquid even when cooled to 0° C., for example, Samples 27F, 27G, 27H, 27J, 27L, 27M, and 27N. Also, phenol mixtures corresponding to Samples 27B, 28B, and 28C are liquid at temperatures between 20° C. and 25° C.

To optimize the relationship between 2-phenylphenol, 4-tert-pentylphenol, and 2-benzyl-4-chlorophenol, these data were further analyzed by Design Expert (Stat-Ease, Inc., Minneapolis, Minn.). The graph generated by this program is shown in FIG. 1. The three-dimensional graph of FIG. 1 shows the melting point of the ternary mixtures of phenolics plotted against the ternary base of weight fraction. The cross-hatched surface shows that melting point varies with the amount of each phenolic compound and that liquid materials can be formed by careful selection of the weight fraction of each phenolic compound. This relationship between the weight fraction of each phenolic compound and the melting point of each mixture can also be described according to the following equation:

$$(55.2x + 83.7y + 33.3z - 182.1xy - 23.7xz + 89xyz) \leq 25$$

in which x is the weight fraction of 2-phenylphenol; y is the weight fraction of 4-tert-pentylphenol; and z is the weight fraction of 2-benzyl-4-chlorophenol. Weight fraction of a component is defined as the weight of that component divided by the sum of the weights of all components. For example, the weight fraction of 2-phenylphenol in Sample 27B is $$\frac{\text{weight of 2-phenylphenol}}{(\text{weight of 2-phenylphenol}) + (\text{weight of 4-tert-pentylphenol}) + (\text{weight of 2-benzyl-4-chlorophenol})} = \frac{1.50 \text{ g}}{1.50 \text{ g} + 0.50 \text{ g} + 0 \text{ g}} = 0.75$$

This weight fraction corresponds to a weight percent of 75%.

The following mixture was also tested according to the standard mixture experiment described and was shown to be useful according to the present invention. 7.06 g 2-phenylphenol (32.8 weight-%); 3.56 g 4-tert-pentylphenol (16.5 weight-%); and 10.9 g 2-benzyl-4-chlorophenol (50.7 weight-%) were mixed and warmed to 55° C. to form a liquid phenolic mixture. When cooled to room temperature (approximately 23° C.), the mixture remained a clear, yellow liquid.

The above specification, examples, and data provide a complete description of the manufacture and use of the compositions and methods of the invention. Because many embodiments can be made without departing from the scope of the invention, the invention resides in the claims hereafter appended.

I claim:

1. A liquid phenolic composition, said composition comprising:

(a) a substituted phenol of the formula:

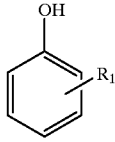

wherein $R_1$ is aryl, aralkyl, $C_{1-24}$ alkyl, or $C_{2-24}$ alkenyl; and (b) a halo-substituted phenol of the formula:

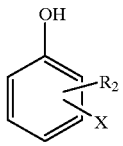

wherein
   $R_2$ is aryl, aralkyl, $C_{1-24}$ alkyl, or $C_{2-24}$ alkenyl; and
   X is halo, wherein said liquid composition is substantially free of a solvent and a surfactant.

2. The composition of claim 1, wherein $R_1$ and $R_2$ are independently phenyl, benzyl, naphthyl, linear $C_{1-12}$ alkyl, or branched $C_{1-12}$ alkyl.

3. The composition of claim 1, wherein said substituted phenol is 2-phenylphenol, 4-phenylphenol, or a mixture thereof.

4. The composition of claim 1, wherein said substituted phenol is 2-tert-pentylphenol, 4-tert-pentylphenol, or a mixture thereof.

5. The composition of claim 1, wherein said composition has a melting point of no greater than 25° C.

6. The composition of claim 1, wherein X is chloro or bromo.

7. The composition of claim 1, wherein said halo-substituted phenol is 2-benzyl-4-chlorophenol, 4-benzyl-2-chlorophenol, or a mixture thereof.

8. The composition of claim 1, wherein said composition comprises phenylphenol and benzylchlorophenol.

9. The composition of claim 1, wherein said composition comprises tert-pentylphenol and benzylchlorophenol.

10. The composition of claim 1, wherein said composition comprises from about 40 to 90 weight-% of said halo-substituted phenol and from about 10 to 60 weight-% of said substituted phenol.

11. The composition of claim 1 further comprising an antioxidant, a wetting agent, a viscosity modifier, a dye, a pH modifier, a fragrance, or a crystallization inhibitor.

12. A liquid phenolic composition, said composition comprising:
(a) a first substituted phenol of the formula:

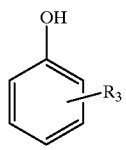

wherein $R_3$ is aryl, aralkyl, $C_{1-24}$ alkyl, or $C_{2-24}$ alkenyl;
(b) a second substituted phenol, different from said first substituted phenol, of the formula:

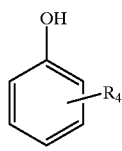

wherein $R_4$ is aryl, aralkyl, $C_{1-24}$ alkyl, or $C_{2-24}$ alkenyl; and
(c) a halo-substituted phenol of the formula:

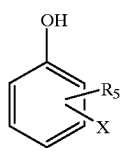

wherein
$R_5$ is aryl, aralkyl, $C_{1-24}$ alkyl, or $C_{2-21}$ alkenyl; and
X is halo,
wherein said liquid phenolic composition is substantially free of a solvent and a surfactant.

13. The composition of claim 12, wherein $R_3$, $R_4$, and $R_5$ are independently phenyl, benzyl, naphthyl, linear $C_{1-12}$ alkyl, or branched $C_{1-12}$ alkyl.

14. The composition of claim 12, wherein at least one of said first substituted phenol and said second substituted phenol is 2-phenylphenol, 4-phenylphenol, or a mixture thereof.

15. The composition of claim 12, wherein at least one of said first substituted phenol and said second substituted phenol is 2-tert-pentylphenol, 4-tert-pentylphenol, or a mixture thereof.

16. The composition of claim 12, wherein said composition has a melting point of no greater than 25° C.

17. The composition of claim 12, wherein X is chloro or bromo.

18. The composition of claim 12, wherein said halo-substituted phenol is 2-benzyl-4-chlorophenol, 4-benzyl-2-chlorophenol, or a mixture thereof.

19. The composition of claim 12, wherein said first substituted phenol is phenylphenol, said second substituted phenol is tert-pentylphenol, and said halo-substituted phenol is benzylchlorophenol.

20. The composition of claim 19, wherein phenylphenol, tert-pentylphenol, and benzylchlorophenol are each present in a weight fraction represented by the following formula:

$$(55.2x+83.7y+33.3z-182.1xy-213.7xz+89.6xyz) \leq 25$$

wherein
x is weight fraction of phenylphenol;
y is weight fraction of tert-pentylphenol; and
z is weight fraction of benzylchlorophenol.

21. The composition of claim 20, wherein the formula is $$(55.2x+83.7y+33.3z-182.1xy-213.7xz+89.6xyz) \leq 10.$$

22. The composition of claim 12 further comprising an antioxidant, a wetting agent, a viscosity modifier, a dye, a pH modifier, a fragrance, or a crystallization inhibitor.

23. A method of forming a liquid phenolic composition, said method comprising:
(a) forming a composition in the substantial absence of a surfactant and in the substantial absence of a solvent, said composition comprising:
(1) a substituted phenol of the formula:

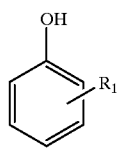

wherein $R_1$ is aryl, aralkyl, $C_{1-24}$ alkyl, or $C_{2-24}$ alkenyl; and
(2) a halo-substituted phenol of the formula:

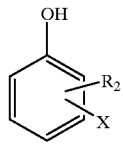

wherein
$R_2$ is aryl, aralkyl, $C_{1-24}$ alkyl, or $C_{2-24}$ alkenyl; and
X is halo; and
(b) mixing said composition to form a liquid composition.

24. The method of claim 23, wherein said mixing step comprises applying heat.

25. The method of claim 23, wherein said mixing step comprises heating the composition to at least 30° C.

26. A method of forming a liquid phenolic composition, said method comprising:
(a) heating in the substantial absence of a surfactant and in the substantial absence of a solvent a substituted phenol of the formula:

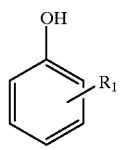

wherein $R_1$ is aryl, aralkyl, $C_{1-24}$ alkyl, or $C_{2-24}$ alkenyl to form a heated liquid substituted phenol;
(b) heating in a substantial absence of a surfactant and in the substantial absence of a solvent a halo-substituted phenol of the formula:

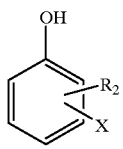

wherein
R$_2$ is aryl, aralkyl, C$_{1-24}$ alkyl, C$_{2-24}$ alkenyl; and
X is halo to form a heated liquid halo-substituted phenol;
(c) combining said heated liquid substituted phenol and said heated liquid halo-substituted phenol to form a heated liquid composition of said substituted phenol and said halo-substituted phenol; and
(d) cooling said heated liquid composition to about ambient temperature to form a liquid phenolic composition.

27. The method of claim 26, wherein said heating step comprises applying heat from a heat-generating device.

28. The method of claim 26, wherein said heating step comprises applying heat through high-shear mixing.

29. The method of claim 26, wherein said heating step comprises heating the composition to at least 30° C.

30. A method of forming a liquid phenolic composition, said method comprising:
(a) forming a composition in the substantial absence of a surfactant and in the substantial absence of a solvent, said composition comprising:
(1) a first substituted phenol of the formula:

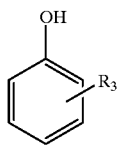

wherein R$_3$ is aryl, aralkyl, C$_{1-24}$ alkyl, or C$_{2-24}$ alkenyl;
(2) a second substituted phenol, different from said first substituted phenol, of the formula:

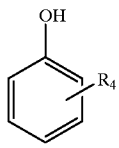

wherein R$_4$ is aryl, aralkyl, C$_{1-24}$ alkyl, or C$_{2-24}$ alkenyl; and
(3) a halo-substituted phenol of the formula:

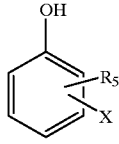

wherein
R$_5$ is aryl, aralkyl, C$_{1-24}$ alkyl, or C$_{2-24}$ alkenyl; and
X is halo; and (b) mixing said composition to form a liquid composition.

31. The method of claim 30, wherein said mixing step comprises applying heat.

32. The method of claim 31, wherein said mixing step comprises heating the composition to at least 30° C.

33. A method of forming a liquid phenolic composition, said method comprising:
(a) heating in the substantial absence of a surfactant and in the substantial absence of a solvent a first substituted phenol of the formula:

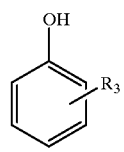

wherein R$_3$ is aryl, aralkyl, C$_{1-24}$ alkyl, or C$_{2-24}$ alkenyl to form a heated liquid substituted phenol;

(b) heating in the substantial absence of a surfactant and in the substantial absence of a solvent a second substituted phenol, different from said first substituted phenol, of the formula:

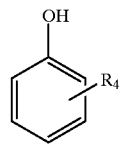

wherein R$_4$ is aryl, aralkyl, C$_{1-24}$ alkyl, or C$_{2-24}$ alkenyl to form a heated liquid second substituted phenol;

(c) heating in the substantial absence of a surfactant and in the substantial absence of a solvent a halo-substituted phenol of the formula:

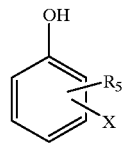

wherein
R$_5$ is aryl, aralkyl, C$_{1-24}$ alkyl, or C$_{2-24}$ alkenyl; and
X is halo
to form a heated liquid halo-substituted phenol;

(d) combining said heated liquid substituted phenol, said heated liquid second substituted phenol, and said heated liquid halo-substituted phenol to form a heated liquid composition of said first substituted phenol, said second substituted phenol, and said halo-substituted phenol; and (e) cooling said heated liquid composition to about ambient temperature to form a liquid phenolic composition.

34. A method of preparing an antimicrobial formulation, said method comprising: incorporating a liquid phenolic composition into a disinfectant formulation, said liquid phenolic composition comprising:

(a) a substituted phenol of the formula:

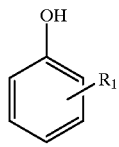

wherein $R_1$ is aryl, aralkyl, $C_{1-24}$ alkyl, or $C_{2-24}$ alkenyl; and (b) a halo-substituted phenol of the formula:

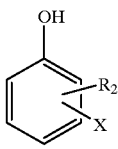

wherein
$R_2$ is aryl, aralkyl, $C_{1-24}$ alkyl, or $C_{2-24}$ alkenyl; and
X is halo,
being substantially free of a solvent and a surfactant, wherein said method produces substantially no phenolic dust and substantially no sensitization in production personnel.

* * * * *